(12) United States Patent
Sharon

(10) Patent No.: US 10,534,007 B2
(45) Date of Patent: Jan. 14, 2020

(54) METHOD FOR THE ASSAY OF SYNUCLEINS

(71) Applicant: YISSUM RESEARCH DEVELOPMENT COMPANY OF THE HEBREW UNIVERSITY OF JERUSALEM, Jerusalem (IL)

(72) Inventor: Ronit Sharon, Mevasseret Zion (IL)

(73) Assignee: YISSUM RESEARCH DEVELOPMENT COMPANY OF THE HEBREW UNIVERSITY OF JERUSALEM LTD, Jerusalem (IL)

(*) Notice: Subject to any disclaimer, the term of this patent is extended or adjusted under 35 U.S.C. 154(b) by 292 days.

(21) Appl. No.: 14/508,114

(22) Filed: Oct. 7, 2014

(65) Prior Publication Data

US 2015/0024419 A1 Jan. 22, 2015

Related U.S. Application Data

(63) Continuation-in-part of application No. PCT/IL2014/050191, filed on Feb. 25, 2014.

(60) Provisional application No. 61/769,586, filed on Feb. 26, 2013.

(51) Int. Cl.
*G01N 33/53* (2006.01)
*G01N 33/92* (2006.01)
*G01N 33/68* (2006.01)

(52) U.S. Cl.
CPC ......... *G01N 33/92* (2013.01); *G01N 33/6896* (2013.01); *G01N 2405/04* (2013.01); *G01N 2800/2835* (2013.01)

(58) Field of Classification Search
CPC ............... G01N 33/92; G01N 33/6896; G01N 2800/2835; G01N 2405/04; G01N 33/57484; G01N 2405/00; G01N 2800/52; G01N 33/53
See application file for complete search history.

(56) References Cited

FOREIGN PATENT DOCUMENTS

| WO | 00/20020 | 4/2000 |
| WO | 2007/089862 | 8/2007 |

OTHER PUBLICATIONS (Sharon et al, 2001, PNAS vol. 98,No. 16, 9110-9115).*

(Continued)

*Primary Examiner* — Julie Wu
*Assistant Examiner* — Carmencita M Belei
(74) *Attorney, Agent, or Firm* — Browdy and Neimark, PLLC

(57) ABSTRACT

The present invention provides a method for the assay of synucleins in a body fluid or tissue sample, wherein said method comprises the steps of contacting said sample with membrane lipids under conditions enabling binding of the synuclein to said lipids, and the detection of the lipid-bound synuclein by a synuclein-binding agent.

16 Claims, 5 Drawing Sheets

(56) References Cited

OTHER PUBLICATIONS

Rudikoff et al (Proc Nati Acad Sci USA 1982 Voi 79 p. 1979).*
Harlow & Lane ("Antibodies: A Laboratory Manual" (1988) ColdSpring Harbor Laboratory Press, Cold Spring Harbor, New York, pp. 25-26).*
Zarbiv et al, Neurobiology of Disease 70 (2014) 90-98.*
Kubo et al (The Journal of Biological Chemistry vol. 280No. 36;issue9,pp. 31664-31-672).*
Hycult Biotech Immunofluorescence Protocol (2010 retrieved from https://www.hycultbiotech.com/media/wysiwyg/protocol_Immunofluorescence.pdf).*
Ketelson et al (Journal of Biological Methods 2008; vol. 339, p. 195-204).*
Martinez et al.(Biochemistry 200, vol. 46, 1868-1877) and Kubo et al.*
Ahmad, et al., γ-Synuclein and the progression of cancer, The FASEB Journal, 2007, pp. 3419-3430, vol. 21.
Antonny, Bruno, Mechanisms of Membrane Curvature Sensing, Annu. Rev. Biochem., 2011, pp. 101-123, vol. 80.
Bosco, et al., Elevated levels of oxidized cholesterol metabolites in Lewy body disease brains accelerate α-synuclein fibrilization, Nature Chemical Biology, May 2006, 249-253, vol. 2(5).
Bruening, et al., Synucleins Are Expressed in the Majority of Breast and Ovarian Carcinomas and in Preneoplastic Lesions of the Ovary, Cancer, May 1, 2000, pp. 2154-2163, vol. 88, No. 9.
Chandra, et al., A Broken α-Helix Folded α-Synuclein, The Journal of Biological Chemistry, Apr. 25, 2003, pp. 15313-15318, vol. 278, No. 17.
Davidson, et al., Stabilization of α-Synuclein Secondary Structure upon Binding to Synthetic Membranes, The Journal of Biological Chemistry, Apr. 17, 1998, pp. 9443-9449, vol. 273, No. 16.
Duda, et al., Neuropathology of Synuclein Aggregates: New Insights Into Mechanisms of Neurodegenerative Diseases, Journal of Neuroscience Research, 2000, pp. 121-127, vol. 61.
Jakes, et al., Identification of two distinct synucleins from human brain, FEBS Letters, 1994, pp. 27-32, vol. 345.
Jo, et al., α-Synuclein Membrane Interactions and Lipid Specificity, Nov. 3, 2000, pp. 34328-34334, vol. 275, No. 44.
Lee, et al., Mechanisms of Parkinson's Disease Linked to Pathological α-Synuclein: New Targets for Drug Discovery, Oct. 5, 2006, pp. 33-38, vol. 52.
Matsuo, et al., Parkinson's Disease-Related Protein, α-Synuclein, in Malignant Melanoma, PLoS One, May 2010, pp. 1-8, vol. 5, issue 5.
Wan Wan, et al., The Role of Alpha-Synuclein Oligomerization and Aggregation in Cellular and Animal Models of Parkinson's Disease, PLoS One, Jun. 2012, pp. 1-14, vol. 7, issue 6.
Zhou, et al., Changes in the solubility and phosphorylation of α-synuclein over the course of Parkinson's disease, 2011, pp. 695-704, vol. 121.
Smith et al., "Formation of High Affinity Lipid-Binding Intermediate during the Early Aggregation Phase of α-Synuclein" Biochemistry, 47:1425-1434 (2008).

* cited by examiner

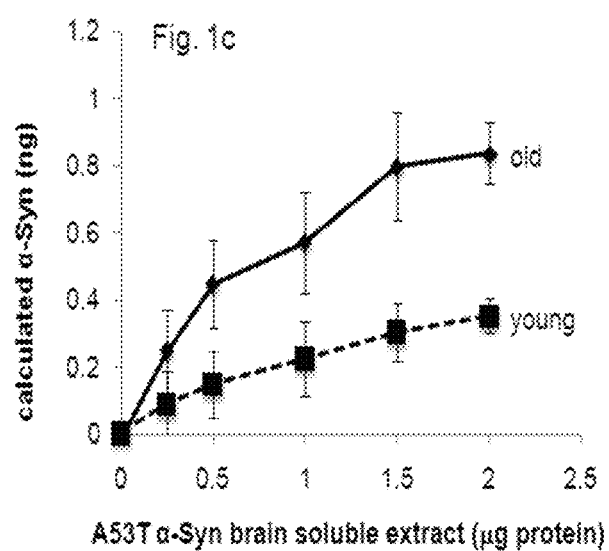

METHOD FOR THE ASSAY OF SYNUCLEINS

FIELD OF THE INVENTION

The present invention relates to a novel, sensitive ELISA assay for the detection of α-Synuclein protein (α-Syn), which may be used as a diagnostic tool for synucleinopathies and other conditions, including certain types of cancer. This method is based on the ability of α-Syn protein to bind membrane lipids.

BACKGROUND OF THE INVENTION

The development of a non-invasive and reliable assay that reflects the pathogenic process is a highly desired objective in the diagnosis and research of Parkinson's disease (PD). Among the different factors associated with the pathogenic process of PD, α-Syn protein is the most prominent factor.

α-Syn is a presynaptic protein critically involved in the cytopathology and genetics of PD (Lee et al., 2006, *Neuron*, 52, 33-38). A progressive conversion of the soluble α-Syn protein into insoluble, β-sheet rich filaments and their intraneuronal deposition into Lewy bodies (LB) and Lewy neurites, underlie its cytotoxicity in the synucleinopathies (Duda et al., 2000, *NeuroSci Res*, 61, 121-127).

Membrane-associated α-Syn has been the focus of many studies. This is primarily because of the findings indicating that upon interactions with membrane phospholipids, the unfolded α-Syn protein acquires an α-helix-rich structure (Davidson et al., 1998, *J Biol. Chem*, 273, 9443-9449). It is hypothesized that the acquisition of structure is critical for the normal function of the protein. Importantly, the acquisition of structure is implicated in α-Syn aggregation and toxicity (Jo et al., 2000, *J. Biol. Chem.* 275, 34328-34334). α-Syn interaction with membranes is dependent on the type of lipids (Jo et al., 2000, *J. Biol. Chem.* 275, 34328-34334), with a preference for anionic head groups and, specifically, phosphatidyl serine (Davidson et al., 1998, *J Biol. Chem*, 273, 9443-9449). α-Syn interactions with membranes involve the N-terminal region of the protein, consisting of residues 1-95 (Antony B 2011, Annu Rev Biochem, 80, 101-123), which harbors six to seven repeats of the conserved KTKEGV motif (Jakes et al. 1994, FEBS Lett, 345, 27-32). This is consistent with an amphipathic helical domain with the polar face having a net positive charge (Chandra et al., 2003, J Biol Chem. 278, 15313-15318) and the preference for anionic phospholipids (Davidson et al., 1998, *J Biol. Chem*, 273, 9443-9449).

Altered levels of synuclein proteins have been detected in the CNS of patients with PD and the related synucleinopathies and also in various types of cancer. For example, α-Syn expression is detected in melanoma tumors and nevi (Matsuo et al., 2010, PLoS One, 5(5)-e10481). Members of the synuclein family were shown to be expressed in breast and ovarian cancer cells (Bruening et al., 2002, *Cancer*, 88, 2154-2163). γ-Syn was found to be overexpressed in ovarian tumors and in ovarian cancer cell lines in contrast to low and almost undetectable levels of γ-syn proteins in the surface epithelial cells of the normal ovary. The expression of γ-syn was seen in 20% of preneoplastic lesions in the ovary, where it showed punctate expression in epithelial inclusion cysts, hyperplastic lesions, and papillary structures.

Furthermore, abnormally high expression of γ-syn has been associated with a wide range of cancer types, including breast, ovarian, cervical, prostrate, liver, pancreatic, colon, gastric, esophagus, and lung compared to almost undetectable levels in adjacent non-neoplastic tissue. In addition to the stage-specific expression of γ-syn, high expression levels in stage III/IV sometimes involving lymph node invasion, was observed in various cancer types. γ-Syn expression is also specifically expressed in high-grade glial tumors such as 33% ependymomas, 63% glioblastomas, and 16% myxopapillary ependymomas, which also demonstrates γ-syn's potential activity as a tumor progression protein is not just restricted to hormone-dependent carcinomas (Ahmad et al. 2007, Faseb J, 21:3419-3430).

Sandwich ELISA methods were recently reported to be a useful diagnostic tool for PD. The sandwich ELISA uses a primary monoclonal anti α-Syn ab for capturing α-Syn antigen from the sample. Then, a general secondary antibody is used for the detection reaction. In addition, a specific sandwich ELISA method was developed to specifically detect oligomeric forms of α-Syn. Specifically, following the initial capturing of α-Syn by the primary monoclonal anti α-Syn ab, the sample is reacted with a polyclonal anti α-Syn ab, that in turn, is used for antigen detection through the HRP-reaction. By using this method it was reported that samples of CSF from PD patients contain a significantly higher ratio of α-Syn oligomers to total α-Syn. In contrast, lower α-Syn levels were found in CSF samples of patients at a progressive state of the disease and drug-naïve patients.

A general disadvantage of the sandwich ELISA method for the detection of α-Syn is that the initial capture step is limited by the specific epitope recognition of the antibody in use. α-Syn undergoes various post translational modifications, including: phosphorylation, ubiquitination, sumoylation, nitrosylation, oligomerization and aggregation. In addition, α-Syn undergoes truncations at its C terminus. Therefore, various α-Syn forms occur in vivo. An additional obstacle is that the physiologic α-Syn forms are yet to be defined and characterized separately from the pathogenic forms of the protein. Therefore, the reliance on a specific antibody, with limited epitope recognition, is a significant disadvantage of this sandwich ELISA method, both with regard to the identification of relevant forms of the protein, and with the level of sensitivity seen with this method.

There is thus a clear need for a highly sensitive assay which can detect and measure α-Syn, even when present at low levels. One purpose of the present invention is to provide such an assay.

A further purpose of the present invention is to use the abovementioned assay for diagnosis of α-Syn-related diseases, determining the severity of said diseases and/or for monitoring a therapeutic regime.

Other aims and purposes will become apparent as the description proceeds.

SUMMARY OF THE INVENTION

The present inventors have developed an improved ELISA method that is based on the intrinsic property of synucleins, such as α-Syn protein, to bind membrane lipids. This property is exploited in order to provide an assay for the functional form of said proteins, that is, the form in which they have become folded into their secondary and tertiary structures, including physiological and pathogenic (toxic) forms of the protein.

The present invention is therefore primarily directed to a method for the assay of synucleins, comprising the steps of contacting said sample with lipids under conditions enabling binding of the synuclein to the lipids, and detection of the lipid-bound synuclein by a synuclein-binding agent. Said synuclein binding agent is preferably an antibody, more preferably a monoclonal antibody.

Preferably the sample is a liquid sample. As will be explained below, the lipids are immobilized, and after contact of the sample with the immobilized lipids, the immobilized complex of synuclein and lipids is separated (for example by washing unbound molecules) and synuclein is detected by a synuclein binding agent.

The binding of the synuclein to the lipids is typically carried out under conditions of physiological pH and physiological concentration of salts.

The term "assay" is used herein to refer to both detection (i.e. the determination of the presence or absence of synucleins in the sample tested) and to the quantitative determination of the concentration of the relevant synuclein in the sample. When a quantitative determination is being performed, the results obtained from the assay of the present invention will be compared with results obtained with standardized amounts of pure synuclein and/or with results obtained from populations of healthy subjects and/or groups of patients having the relevant disease. In some cases, the results obtained with a patient's sample will be compared with average values obtained from a standard set of results previously obtained from a cohort of patients. In many cases (for example, when the assay is being used for diagnostic purposes), the results obtained with the patient's sample will be compared with a threshold value previously obtained from a standard set of results. A positive diagnosis (i.e. presence of the disease) is reached when the results obtained with the patient's sample is significantly different from the previously-determined threshold value. In most such cases, a positive diagnosis will be obtained when the synuclein concentration measured in the patient's sample is significantly higher than the reference value. However, in certain instances, a significant reduction in synuclein concentration (when compared with the reference value) will be used as the indicator of the presence of the disease.

In accordance with the invention the synuclein is selected from alpha, beta and gamma synuclein.

In a highly preferred embodiment, the synuclein to be detected and measured is α-Syn.

Typically, the lipids are of the kind that present in biological membranes or form membrane structures (including micelles, vesicles, liposomes emulsion etc.) in vitro, although when immobilized in the method of the invention they may not present as fully functioning biological membranes. When the lipids are of a natural source, in accordance with a preferred embodiment of the invention, they are of the type that can be found in naturally occurring biological membranes. Alternatively, synthetic lipids may be used. As indicated above preferably the lipids are immobilized prior to the assay.

Typically, the membrane forming lipids are naturally occurring, purified or synthetic phospholipids, sphingolipids, plasmalogens, triglycerides, cholesterol, glycolipids or free fatty acids, or a combination of two or more of the above. In accordance with a preferred embodiment of the invention the combination of two or more lipids is used.

The naturally occurring or synthetic phospholipids, plasmalogens and ether-phospholipids, sphingolipids, cholesterol and glycolipids are selected from the group consisting of: phosphatidyl inositol, phosphatidyl serine, phosphatidic acid, phosphatdylethanolamine, phosphatidylcholine, phosphatidylserine, phosphatidylglycerol, phosphatidylinositol, phosphoinositides, such as phosphatidylinositol 4, bisphosphate (PI4P) or any PIP of the seven different molecules, cardiolipin, ceramide, sphingomyelin, glucosylcerebrosidase, galactosylceramide, lactosylceramide, gangliosides, cholesterol, cholesterol-ester, triglycerides, diglycerides and monoglycerides.

The acyl side chains of these lipids may include saturated, unsaturated or poly unsaturated fatty acids. The carbon chain length of the fatty acyl chain may vary between 2-40 carbons for the fatty acid.

Preferably the membrane forming lipids comprise a combination of a phosphoinositide (such as phosphatidyl inositol) and phosphatidyl serine.

In a non-limiting example the ratio of the phosphoinositide (such as phosphatidyl inositol) to phosphatidyl serine is from 10:1 to 1:10, preferably 1:2 or 1:1.

Preferably, the lipids used in the assay comprise purified myelin and/or cellular membrane fractions and/or purified lipoproteins including apolipoproteins and/or extracts of adipose tissue.

Preferably, the lipids are obtained from animal, plant, algal, fungal and bacterial sources.

In accordance with a preferred embodiment of the invention prior to contact with the immobilized membrane-forming lipids the sample may optionally be pretreated at a temperature of 30-85° C., preferably about 65° C., for a period of 10-72 hours, preferably about 16 hours.

In another preferred embodiment of the present invention the sample is pretreated with Proteinase K, prior to being contacted with the lipids.

Typically, a synuclein binding agent, such as an antibody used to identify the lipid-bound synuclein. Preferably, the antibody that binds synuclein is of a first species and is detected by using another labeled antibody from a second species.

In the method according to the invention, the sample tested may be selected from the group consisting of samples of brain biopsy, skin, salivary glands, intestine or tumor biopsy as well as liquid extracts from tumor biopsies, CSF, saliva, erythrocytes, whole blood, serum, erythrocytes plasma, urine, lymph, sputum, extracts of cultured cells and human or laboratory animal tissues or extracts.

In one preferred embodiment, the sample to be tested is saliva. In another preferred embodiment, the sample contains erythrocytes. In such embodiments, said erythrocyte-containing sample may be obtained from whole blood, and may also contain platelets.

The assay of the invention may be used for the detection or diagnosis of a disease, for determining the severity of diseases, or for monitoring a therapeutic regime. The severity of the disease being diagnosed and/or the progress of a therapeutic regime being monitored are determined by the use of calibration curves generated with known amounts of purified, recombinant synuclein, or by the use of calibration curves obtained with data obtained from healthy control subjects and/or patients having the relevant disease.

The disease to be detected or diagnosed may be any type of synucleinopathy or cancer.

For detection purposes, the method of the invention may be used for detection of a synucleinopathy or cancer in an individual from which the sample was obtained, wherein the level of immobilized α-Syn (immobilized to the lipids) is compared to one or more reference values obtained from groups of healthy individuals and/or patients diagnosed with the relevant synucleinopathy or cancer. A level in the tested sample, which is significantly different from the reference value(s), indicates the presence of synucleinopathy or cancer in the individual from which said sample was obtained.

The assay of the present invention enables the determination of levels of immobilized α-Syn, the ratio between immobilized and non-immobilized α-Syn, as well as the determination of the levels of immobilized α-Syn before and after pretreatment with Proteinase K (or any other enzymatic or chemical digestion).

Without wishing to be bound by theory, it is believed that the proteinase K-resistant form of α-Syn (and of other synucleins) is the pathogenic form implicated in various synucleinopathies and cancerous conditions. Thus, in one aspect of the method of the present invention, said method is used to determine the ratio of total synucleins (of the type or class being measured) to proteinase K-resistant synucleins. In this embodiment, the above-disclosed method further comprises pretreating a separate aliquot of the biological fluid sample with proteinase K, repeating all of the steps of said method using said aliquot, and calculating the ratio of the synuclein concentration in the original, untreated sample to the synuclein concentration in said proteinase K pretreated sample, wherein said ratio represents the ratio of total synucleins to proteinase K-resistant synucleins.

As indicated above, the method of the invention may be used for determining the severity of a specific synucleinopathy or specific cancer in an individual from which a sample was obtained, wherein the detected level of α-Syn is compared to that of levels in samples obtained from patients with known severity of the specific synucleinopathy or specific cancer.

For monitoring therapy, the method of the invention may be used for monitoring the effect of anti-synucleinopathy therapy or anti-cancer therapy, wherein changes in the levels of the detected α-Syn are monitored during therapy.

In accordance with the present invention, the synucleinopathy may be selected from the group consisting of PD, including PD with dementia (PDD); Lewy body dementia Alzheimer's disease, multiple system atrophy, NIEMANN-PICK-type 1, and neuro-degeneration with brain iron accumulation-1. In addition, the above methods may be used for detection or monitoring of cancer, comprising melanoma and other skin-type cancers, breast, prostate, colon, brain, kidney and lung cancers.

In another aspect, the present invention is directed to a kit containing some or all of the substances, components and agents required to perform the ELISA technique disclosed hereinabove, wherein said kit may be used to measure the concentration of synucleins in a sample. In one preferred embodiment, said kit comprises immobilized lipids capable of binding said synucleins and least one anti-synuclein antibody. In another preferred embodiment, the kit further comprises a second antibody labelled with a visible label or tag, such as horseradish peroxidase. In still further preferred embodiments, the kit of the present invention will further comprise additional reagents and buffers that are needed to perform the assay, and may optionally also comprise a set of instructions for using said kit.

In another embodiment, the kit further comprises proteinase K, in order to determine the ratio between lipid bound proteinase-resistant synuclein and total lipid bound synuclein

BRIEF DESCRIPTION OF THE DRAWINGS

FIG. 1a demonstrates the results in an assay in which the concentration of recombinant α-Syn protein is measured, while the results in FIG. 1b were obtained using α-Syn protein from tg brain extracts.

FIG. 1c represents the difference in capture of normal and pathogenic α-Syn, originating from healthy and sick mouse brains, respectively.

FIG. 4a presents the total α-Syn levels determined by phospholipid ELISA assay in healthy control (HC; n=17); PD (n=21); and PD patients with implanted deep brain stimulation (DBS) electrodes (n=12). Similarly, FIG. 4b presents the levels of PK-resistant α-Syn, while FIG. 4c presents the ratio of total-to-proteinase K-resistant α-Syn for the three subject groups.

DETAILED DESCRIPTION OF PREFERRED EMBODIMENTS

Figure 1:
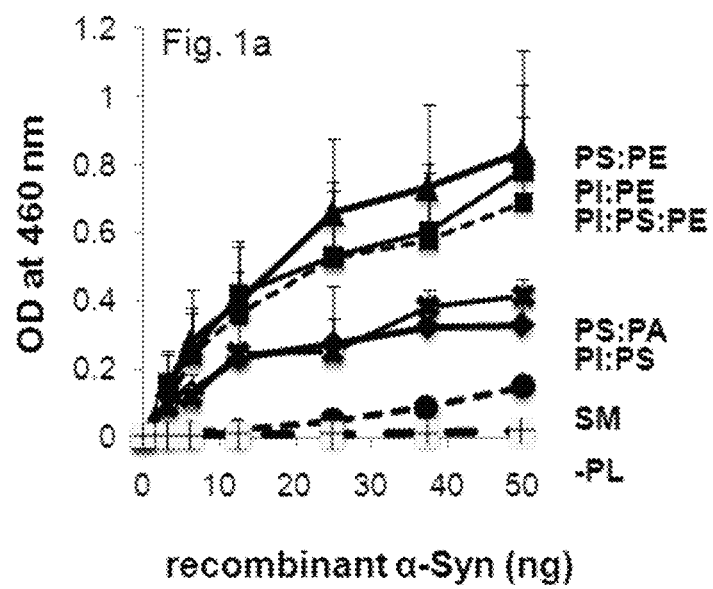
FIG. 1 graphically compares the effect of combinations of different lipids on α-Syn detection by means of the ELISA assay of the present invention.
Figure 1:
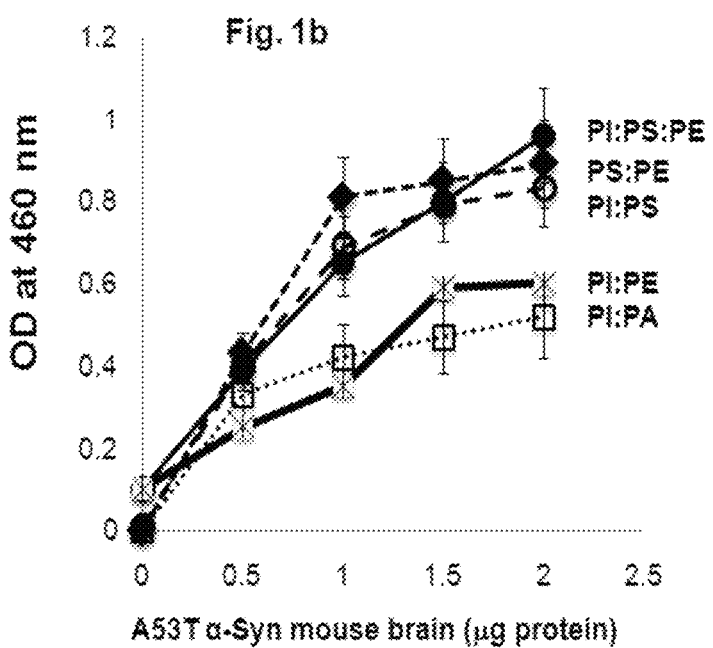

As explained hereinabove, a key inventive feature of the present invention is the fact that the ELISA assay disclosed and claimed herein is based on the measurement of synucleins whilst bound to membrane lipids and separated from the non-bound components of the sample. These proteins essentially lack secondary and tertiary structure when present in their free cytosolic, unbound form, and only adopt their functional, folded forms upon binding to lipids.

In addition, the present invention also includes within its scope the determination of the ratio of the concentration of lipid-bound α-Syn to the total concentration of α-Syn (i.e. including unbound α-Syn).

In accordance with one option the invention also includes within its scope the determination of the ratio of lipid bound proteinase K-resistant bound α-Syn to the total concentration of lipid bound α-Syn Without wishing to be bound by theory, the use of membrane proteins in the presently-disclosed ELISA to bind the synucleins that are present in the sample being tested, leads to at least the following two novel and unexpected advantages of the present invention:

a) The form of the synuclein being assayed is the functionally-relevant (and hence pathogenically-relevant) form of the protein which by one option is lipid bound and by another option is both lipid bound and proteinase K resistant form;

b) Epitope recognition by the antibodies used in the ELISA is enhanced following folding of the proteins (possibly by creation of new three-dimensional binding sites), thereby leading to greatly-enhanced sensitivity, and reduced minimal threshold detection values.

In accordance with a preferred embodiment of the invention, prior to contact with the immobilized membrane-forming lipids the sample may optionally be pre-incubated at a temperature of 30-100° C., preferably about 65° C., for a period of 10-72 hours. Such a treatment increases the sensitivity of the assay.

In a more preferred embodiment of this aspect of the invention, the sample is pretreated at a temperature of 30-85° C. for a period of 16 hours.

In a still more preferred embodiment of the method of the invention, the sample is pre-treated at a temperature of 65° C. for a period of 16 hours.

In accordance with another preferred embodiment, the sample is treated with PK prior to the assay. In one preferred embodiment of this aspect of the invention, the PK treatment is performed for 30 minutes at 37° C. Preferably, the PK is used at concentrations in the range of 0-10 µg/ml, The sample to be assayed may be taken from any convenient biological fluid or liquid extract of a tissue, biopsy or cell sample. In one preferred embodiment, however, the sample is selected from the group consisting of CSF, saliva, erythrocytes, platelets, whole blood, serum, plasma, urine, lymph, sputum, brain, skin, intestine, salivary gland or tumor biopsy, extracts of cultured cells and human or laboratory animal tissue.

In one preferred embodiment of the method of the invention, the sample is saliva.

In another preferred embodiment the sample is a sample of erythrocytes, or a mixture of erythrocytes and platelets.

In accordance with one embodiment of the invention, the method is used for diagnosis of synucleinopathies, selected from the group consisting of PD, dementia with LB, Alzheimer's disease, multiple system atrophy, NIEMANN-PICK-type 1 and neuro-degeneration with brain iron accumulation-1.

In accordance with another embodiment of the invention, the method is used for the detection or monitoring of cancer. In one preferred embodiment the cancer to be detected and/or monitored is melanoma. Additional relevant cancer types include (but are not limited to) other skin-type cancers, as well as cancers of the breast, prostate, colon, brain, kidney and lung.

In accordance with a further embodiment of the invention, the method is used for determination of the severity of the disease.

In accordance with a still further embodiment of the invention, the method is used for monitoring a therapeutic regime.

In another aspect, the invention also encompasses a kit for measuring the concentration of synucleins in a sample, wherein said kit may be used for the diagnosis of synucleinopathy-related diseases and/or cancer, and or for the monitoring of disease progression or the effect of a treatment regime. Said kit preferably comprises immobilized lipids to which the synucleins are capable of binding, and least one anti-synuclein antibody. Generally, the kit will also comprise a second antibody labeled with a visible tag, for example Horseradish peroxidase (HRP). In a preferred embodiment of this aspect of the invention, the synuclein to be detected and/or measured is α-Syn. In one preferred embodiment, the kit further comprises proteinase K.

EXAMPLE 1

Phospholipid-ELISA Assay

The effect of different lipid combinations on α-Syn detection by the ELISA assay was tested. The phospholipids used in this study were: sphingomyelin (SM), phosphatidic acid (PA), phosphatidyl inositol (PI), phosphatidyl serine (PS), cholesterol and free fatty acids. The final concentration of the lipids used was in the range of 100-300 µg lipids/well, and ratios between the different lipids of 1:1; 1:2 and 1:3 were tested.

The efficacy of the method in detecting purified recombinant α-Syn (FIG. 1a), human α-Syn present in brain extracts of transgenic mice (FIG. 1b), or α-Syn in young and healthy versus old and symptomatic A53T α-Syn transgenic (tg) mice (FIG. 1c) was shown. Samples of brain homogenates (0-3.5 µg) were tested with different phospholipids compositions: PI/PE (1:1), PI/PS (1:1), PE/PS (1:1), PS:PA (1:1), SM PI/PS/PE (1:1:1) or without any phospholipids.

Methods and Materials:

Phospholipid ELISA assay. A PolySorp, 96-well ELISA plate (Thermo Scientific) was coated with a mixture of phospholipids dissolved in methanol in a final amount of 100 µg/well and incubated overnight at 4° C. for complete evaporation of methanol. Blocking was performed with 100 µl/well of 1% BSA (fatty acid-free, Calbiochem) in PBS for one hour at 37° C., followed by one wash with PBS. Samples at a final volume of 100 µl/well were added: Purified human α-Syn at 0-50 ng/well, in triplicate; the soluble fraction of A53T α-Syn tg, ntg or α-Syn-/-mouse brain at 0-2.5 µg protein/well. Plates were incubated for 3 hours at 37° C. Following incubation, samples were removed and the wells were washed 4 times with PBS. A mouse anti-α-Syn antibody (α-Syn#10) was diluted 1:10,000 in 1% BSA in PBS. Following incubation for one hour at 37° C., the wells were washed 3 times and incubated for one hour at 37° C. with the HRP-conjugated donkey anti-mouse secondary antibody at 1:8000 (Jackson Laboratories). Following 3 washes with PBS, 50 µA of TMB one component micro-well substrate (SouthernBiotech, Birmingham, Ala., USA) were added per well. The reaction was terminated with 50 µl/well of 1M $H_2SO_4$. Absorbance at 450 nm was determined using a plate reader (EL808 Ultra Microplate Reader, Bio-Tek Instruments, Vt., USA). The amount of α-Syn was determined for each plate according to a standard curve using recombinant α-Syn performed in parallel to the tested samples.

Samples of blood, collected in anti-coagulant tube (2-5 ml) were spun down at 2,200 rpm at room temperature for 10 minutes. The plasma was removed and cell pellet washed in PBS in 1:1 volume and spun again at 1000 rpm for 10 minutes. Cells are lysed osmotically in the presence of cold DDW, incubated for 5 minutes on ice. The osmolytes in the samples were adjusted to 1×PBS (with a 10× concentrated solution) and spun at 17,000 rpm, 4 degrees for 30 minutes. The supernatant was collected and assayed.

Results:
1. The combination of PE:PS at 1:2 with 100 µg/well yielded the best result for the recombinant α-Syn protein (FIG. 1a). The combination of PI:PS:PE at 1:1 ratio yielded the best results for the α-Syn tg brain extracts (FIG. 1b).
2. The effect of the different lipid composition on α-Syn detection—the results indicate differences between capture of α-Syn originating from the healthy (young mouse brain, with no indications for α-Syn pathology) or sick (old mouse brain with profound α-Syn pathology detected by histopathology) mouse brains. These differences in capture represent different binding preferences for the normal vs. pathogenic-α-Syn (FIG. 1c).

These results indicate that the lipid-binding ELISA assay of the present invention may be used with different lipid combinations in order to detect and quantify α-Syn in biological samples.

EXAMPLE 2

Effect of Proteinase K (PK) Pretreatment

Materials and Methods:

To differentiate normal and pathogenic α-Syn in human erythrocytes, the sample was treated with increasing concentrations of PK at the indicated concentrations for 30 minutes at 37° C., prior to the analysis by phospholipid-bound ELISA. The PK-resistant form of α-Syn is considered to be the pathogenically-involved form.

Figure 2:
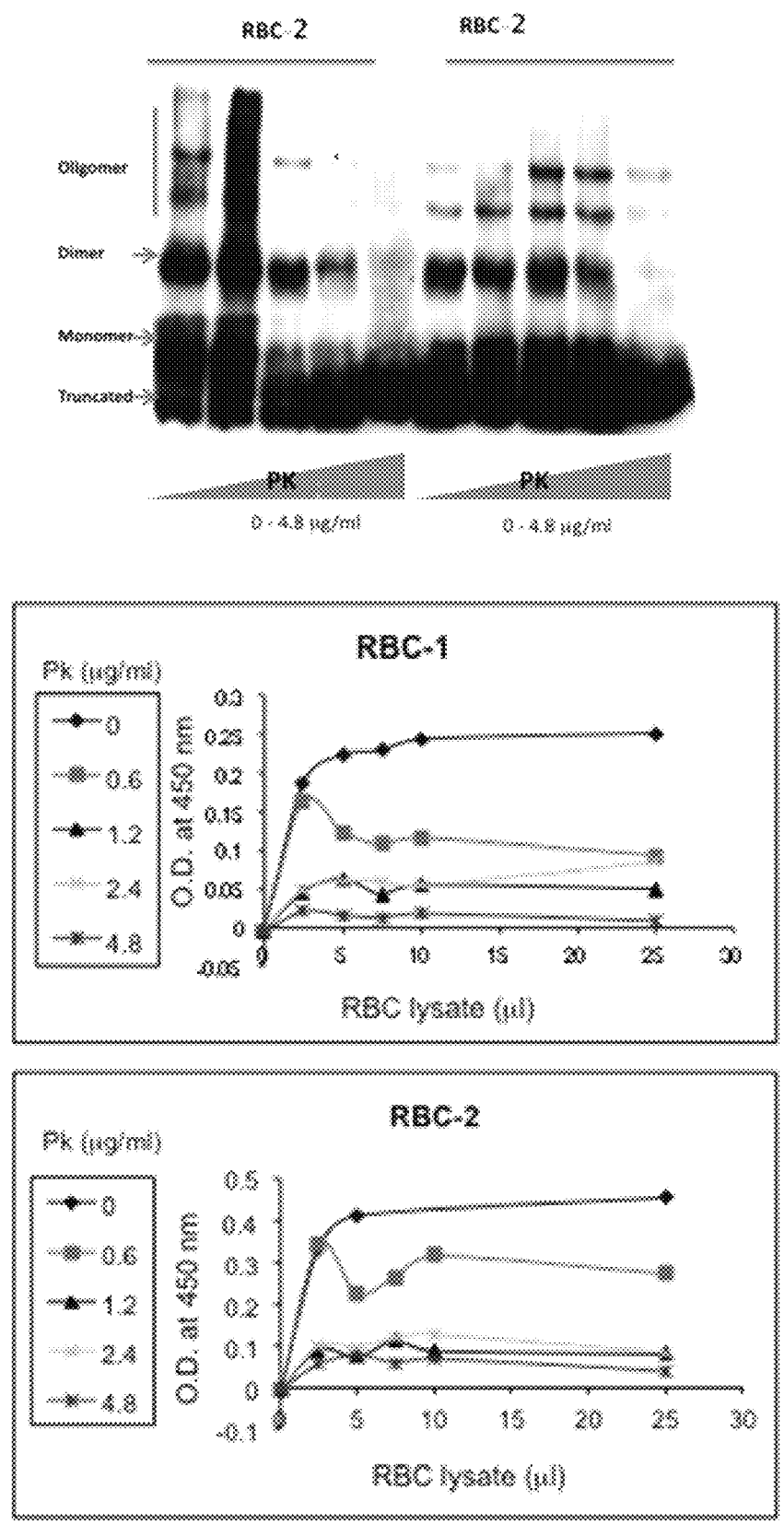
FIG. 2 graphically illustrates the analysis of α-Syn in extracted human erythrocytes by western blotting and phospholipid-ELISA. The figure shows α-Syn protein in samples of erythrocytes and platelets, following incubation with increasing concentrations PK for 30 minutes at 37° C. The resistance of α-Syn in the sample for PK treatment is seen in the Western blot results.

Results:

FIG. 2 graphically illustrates the analysis of extracted human erythrocytes for α-Syn by western blotting and phospholipid-ELISA, in parallel. The figure represents the samples of erythrocytes with increasing concentrations of PK.

It may be seen from the western blot results shown in the left side of the figure, that the higher concentrations of PK lead to more specific detection of the non-aggregated forms of synuclein in erythrocytes, thus enabling better differentiation between normal and pathogenic synuclein, thereby improving the specificity of the assay.

EXAMPLE 3

The use of the ELISA assay of the present invention in the diagnosis of Parkinson's disease Materials and Methods:

19 subjects with PD were compared to a group of 15 age-matched healthy control subjects. The experiment was performed blinded for group identity, in collaboration with the Neurology department at Hadassah Medical Center. The amount of α-Syn was determined in samples of red blood cells, according to a standard curve created with known amounts of purified α-Syn protein. Separate assays using the lipid-binding ELISA assay of the present invention were performed for PK pretreated samples, and for samples that had not undergone such pretreatment. The assays were performed essentially as described in the materials and methods section of Example 1, hereinabove. The lipid mixture used to coat the multi-plate wells comprised of PI:PS:PE (1:1:1).

Figure 3:
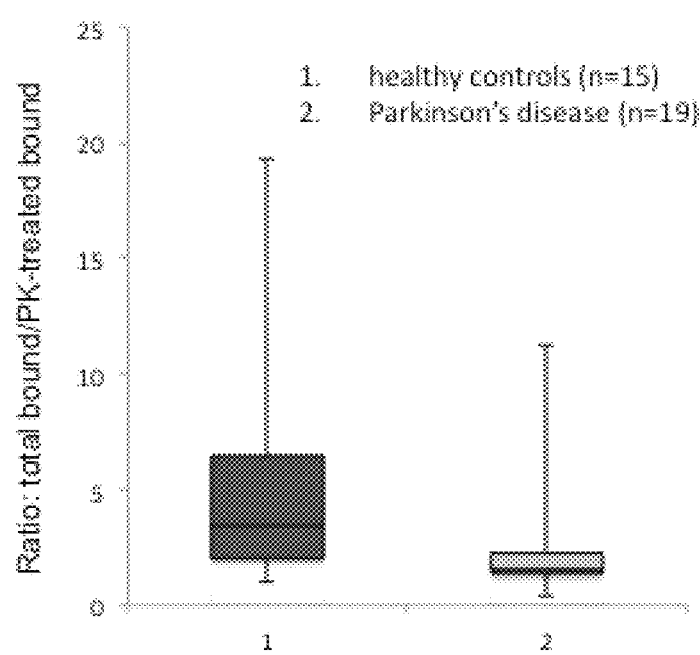
FIG. 3 graphically presents results of the phospholipid-ELISA method in subjects with PD (2) (n=19) and age-matched healthy control groups (1) (n=15), and demonstrates that the method is a useful diagnostic tool for PD. The results presented in the graph are expressed as the ratio of total α-Syn to PK-resistant α-Syn.

Results:

FIG. 3 graphically presents the results of the assays described above. These results are expressed as the ratio of total α-Syn to PK resistant α-Syn detected by the method. The two groups were found significantly different (t-test, P value>0.01). It may be seen that the fraction of PK resistant synuclein is significantly higher in PD patients compared to healthy control (i.e. the ratio of total of α-Syn to PK resistant α-Syn is lower). Since the PK resistant form of the protein is recognized to be the pathogenic form for conditions such as PD, these results clearly indicate that the phospholipid-ELISA method described herein is an accurate and sensitive diagnostic tool for said disease.

EXAMPLE 4

Levels of Proteinase K Resistant α-Syn in RBCs in Healthy Controls Versus PD Groups The ratio of total-to-proteinase K (PK) resistant lipid bound α-Syn detected in samples of red blood cells (RBCs) from patients with PD and healthy controls was tested. The detection of total and proteinase K-resistant α-Syn was performed using a phospholipid-ELISA assay as described above.

Materials and Methods:

21 subjects with PD were compared to a group of 12 PD patients treated with implanted Deep brain stimulation (DBS) and 17 age-matched healthy control subjects.

The experiment was performed blinded for group identity, in collaboration with the Neurology department at Hadassah Medical Center.

The amount of lipid bound α-Syn (ng/μl) was determined in samples of RBCs using the phospholipid ELISA assay disclosed hereinabove. Separate assays were performed for PK pretreated samples, and for samples that had not undergone such pretreatment. The assays were performed essentially as described in the materials and methods section of Example 1, hereinabove. One-way analysis of variance (ANOVA) was used to determine whether there are any significant differences between the means of two or more independent (unrelated) groups.

Figure 4:
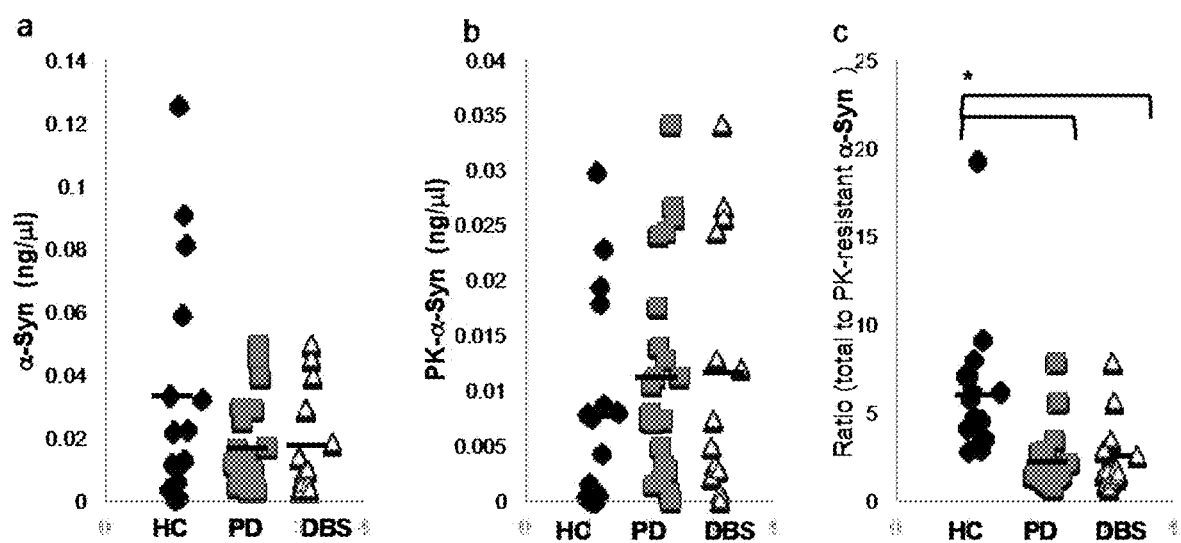
FIG. 4 graphically compares levels of α-Syn in RBCs of healthy controls and two separate PD groups.

Results:

The results are presented in FIG. 4, which shows the levels of α-Syn (ng/μl) in RBCs of healthy controls and the two PD groups.

FIG. 4a graphically compares total lipid bound α-Syn levels determined by phospholipid ELISA assay in healthy controls (HC; n=17), PD (n=21) and PD patients with implanted DBS (n=12). The results clearly indicate a higher mean value of the total α-Syn level in RBCs samples from healthy controls as opposed to PD groups.

FIG. 4b shows PK-resistant lipid bound α-Syn concentrations determined by the phospholipid ELISA assay. It may be seen from this figure that the level of PK resistant synuclein in samples of RBCs is significantly higher in PD patients compared to healthy control.

The results presented in FIG. 4c are expressed as the ratio of total-to-proteinase K-resistant lipid bound α-Syn detected by the method of the present invention. The statistical significance of the difference between the results obtained for the various groups was assessed using one way ANOVA. The results indicate a significantly higher ratio of total α-Syn to PK resistant α-Syn in the healthy control groups as opposed to the two PD groups (p=0.011).

It may be concluded from these results that pathogenic forms of α-Syn—that is forms characterized by their resistance to proteinase k digestion—occur in RBCs at higher levels in PD patients (either with or without implantation of DBS) than in the healthy controls.

The invention claimed is:

1. A method for assaying synucleins in a sample of a biological fluid, comprising:
    immobilizing synuclein-binding lipids onto a solid support,
    bringing said sample into contact with the immobilized synuclein-binding lipids, under conditions enabling binding of synuclein in the sample to said immobilized synuclein-binding lipids, thereby forming an immobilized complex of said synuclein and synuclein-binding lipids;
    washing away unbound molecules;
    contacting the immobilized complex with an synuclein specific antibody that binds to the lipid-bound synuclein; and
    detecting the lipid-bound synuclein,
    wherein the synuclein is selected from the group consisting of alpha synuclein and beta synuclein.

2. The method according to claim 1, for assaying α-synuclein in a sample of a biological fluid, wherein said detecting step comprises detecting α-synuclein bound to the immobilized lipids.

3. The method according to claim 1, wherein the synuclein-binding lipids are selected from the group consisting of synuclein-binding naturally occurring, purified or synthetic phospholipids, glycolipids, plasmalogenes, sphingolipids, cholesterol, glycolipids and combinations thereof.

4. The method according to claim 3, wherein the synuclein-binding lipids are selected from the group consisting of phosphatidyl inositol, phosphatidyl serine phosphatidic acid, phosphatidylethanolamine, phosphatidylcholine, phosphatidylserine, phosphatidylglycerol, phosphoinositides, cardiolipin, ceramide, sphingomyelin, ether-phospholipids, glucosylcerebrosidase, galactosylceramide lactosylceramide, gangliosides, cholesterol, cholesterol-ester, triglycerides, diglycerides, monoglycerides, and combinations thereof.

5. The method according to claim 4, wherein the synuclein-binding lipids are a combination of one or more phosphoinositides, phosphatidyl ethanolamine and phosphatidyl serine.

6. The method according to claim 5, wherein the ratio of phosphoinositide to phosphatidyl serine is from 10:1 to 1:10.

7. The method according to claim 1, wherein the sample is heated at a temperature of 30-85° C. prior to contact with the immobilized synuclein-binding lipids.

8. The method according to claim 1, wherein the sample is pretreated with Proteinase K, prior to contact with the immobilized synuclein-binding lipids.

9. The method according to claim 1, wherein the antibody capable of binding to lipid-bound synuclein is of a first species and is detected by using another labeled antibody from a second species.

10. The method according to claim 1, wherein the biological fluid sample is selected from the group consisting of CSF, saliva, erythrocytes, platelets, whole blood, serum, plasma, urine, lymph, sputum, brain extracts, skin extracts, intestine extracts, salivary gland extracts, tumor biopsy extracts, extracts of cultured cells and human or laboratory animal tissue.

11. The method according to claim 10, wherein the biological fluid sample is saliva.

12. A method for determining the ratio of total lipid bound synucleins to proteinase K-resistant lipid bound synucleins in a sample of a biological fluid comprising:
(A) dividing the liquid sample into a first and second separate aliquots,
(B) performing the method of claim 1 on the first aliquot to determine the total lipid-bound synuclein concentration,
(C) pretreating the second aliquot with proteinase K,
(D) performing the method of claim 1 on the proteinase K pre-treated second aliquot to determine the proteinase K resistant lipid-bound synuclein concentration in the second aliquot; and
(E) calculating the ratio of the total lipid-bound synuclein concentration obtained in step (B) to the lipid-bound synuclein concentration in said proteinase K pre-treated sample obtained by step (D), wherein said ratio represents the ratio of total lipid bound synucleins to proteinase K-resistant lipid-bound synucleins.

13. A method for the detection of a synucleinopathy or cancer in an individual using the method of claim 1, comprising:
(A) performing the method of claim 1 with a biological fluid sample obtained from the from an individual suspected of having synucleoinopathy or cancer,
(B) performing the method of claim 1 with biological fluid samples obtained from groups of healthy individuals,
(C) comparing the amount of synuclein bound to the immobilized lipid detected in the biological fluid sample in step (A) with the amount of synuclein bound to the immobilized lipid detected in biological fluid samples of step (B); and
(D) identifying that the individual as having synucleinopathy or cancer when the amount of synuclein bound to the immobilized lipid of step (A) is significantly different from the amount of synuclein bound to the immobilized lipid detected in step (B).

14. A method for determining the severity of a specific synucleinopathy or cancer in an individual, comprising:
(A) Performing the method of claim 1 with a biological fluid sample obtained from the from an individual with synucleinopathy or cancer;
(B) performing the method of claim 1 with biological fluid samples obtained from patients with known severity of synucleinopathy or cancer to determine one or more reference values, wherein one or more reference values representing the levels of synuclein bound to the immobilized lipid in biological fluid samples obtained from patients with known severity of synucleinopathy or cancer
(C) determining the severity of the synucleinopaty or cancer by comparing the amount of synuclein bound to the immobilized lipid detected in step (A) with one or more of the reference values obtained in step (B).

15. A method for monitoring the effect of anti-synucleinopathy therapy or anti-cancer therapy conducted on an individual, comprising:
administering an anti-synucleinopathy therapy or anti-cancer therapy to an individual diagnosed with a synucleinopathy or cancer,
performing the method of claim 1 in fluid samples obtained from the individual during different points during the course of therapy,
determine the amount of lipid-bound synuclein during the course of therapy,
comparing the amount of lipid-bound synuclein detected during different points during the course of therapy.

16. A method in accordance with claim 1, wherein said immobilized lipids are immobilized in wells, as a coating thereon.

* * * * *

UNITED STATES PATENT AND TRADEMARK OFFICE
CERTIFICATE OF CORRECTION

PATENT NO. : 10,534,007 B2
APPLICATION NO. : 14/508114
DATED : January 14, 2020
INVENTOR(S) : Ronit Sharon et al.

It is certified that error appears in the above-identified patent and that said Letters Patent is hereby corrected as shown below:

In the Claims

At Claim 13, Column 12, Line 8, delete "from the";

At Claim 14, Column 12, Line 26, delete "from the"; and

At Claim 14, Column 12, Line 35, insert --; and-- after "cancer".

Signed and Sealed this
Second Day of June, 2020

Andrei Iancu
*Director of the United States Patent and Trademark Office*